(12) United States Patent
Backes

(10) Patent No.: US 8,082,783 B2
(45) Date of Patent: Dec. 27, 2011

(54) OPTICAL SENSOR DEVICE

(75) Inventor: Ulrich Backes, Radolfzell (DE)

(73) Assignee: TRW Automotive Electronics & Components GmbH, Radolfzell (DE)

( * ) Notice: Subject to any disclaimer, the term of this patent is extended or adjusted under 35 U.S.C. 154(b) by 48 days.

(21) Appl. No.: 12/620,622

(22) Filed: Nov. 18, 2009

(65) Prior Publication Data

US 2010/0147067 A1 Jun. 17, 2010

(30) Foreign Application Priority Data

Dec. 11, 2008 (DE) .......................... 10 2008 061 616

(51) Int. Cl.
*G01W 1/00* (2006.01)
(52) U.S. Cl. ..................................... 73/170.17
(58) Field of Classification Search .................. None
See application file for complete search history.

(56) References Cited

U.S. PATENT DOCUMENTS

| | | | | |
|---|---|---|---|---|
| 5,313,072 A | * | 5/1994 | Vachss | 250/573 |
| 5,661,303 A | * | 8/1997 | Teder | 250/341.8 |
| 5,898,183 A | * | 4/1999 | Teder | 250/574 |
| 6,108,084 A | | 8/2000 | Winner | |
| 2004/0027666 A1 | | 2/2004 | Sautter | |
| 2007/0235638 A1 | | 10/2007 | Backes et al. | |
| 2008/0116379 A1 | * | 5/2008 | Teder | 250/341.1 |
| 2008/0297803 A1 | | 12/2008 | Backes | |
| 2009/0261237 A1 | * | 10/2009 | Backes | 250/227.11 |

FOREIGN PATENT DOCUMENTS

| | | |
|---|---|---|
| DE | 19530289 | 2/1997 |
| DE | 19701258 | 7/1997 |
| DE | 19830120 | 2/1999 |
| DE | 10132889 | 1/2003 |
| DE | 102006039065 | 3/2007 |
| DE | 202006005665 | 9/2007 |
| DE | 102007039349 | 2/2009 |

\* cited by examiner

*Primary Examiner* — Andre Allen
(74) *Attorney, Agent, or Firm* — Tarolli, Sundheim, Covell & Tummino LLP

(57) ABSTRACT

An optical sensor device that can be used as a rain sensor has a light emitter, a light receiver, and an optical plate with rotationally symmetrically shaped Fresnel prism structures, which is coupled to a pane, in particular a windshield of a vehicle, by means of a coupling layer. On its opposite side, the optical plate takes up light from the light emitter. The light is coupled into the pane and, after a total reflection on an internal surface of the pane, is directed onto the light receiver.

18 Claims, 6 Drawing Sheets

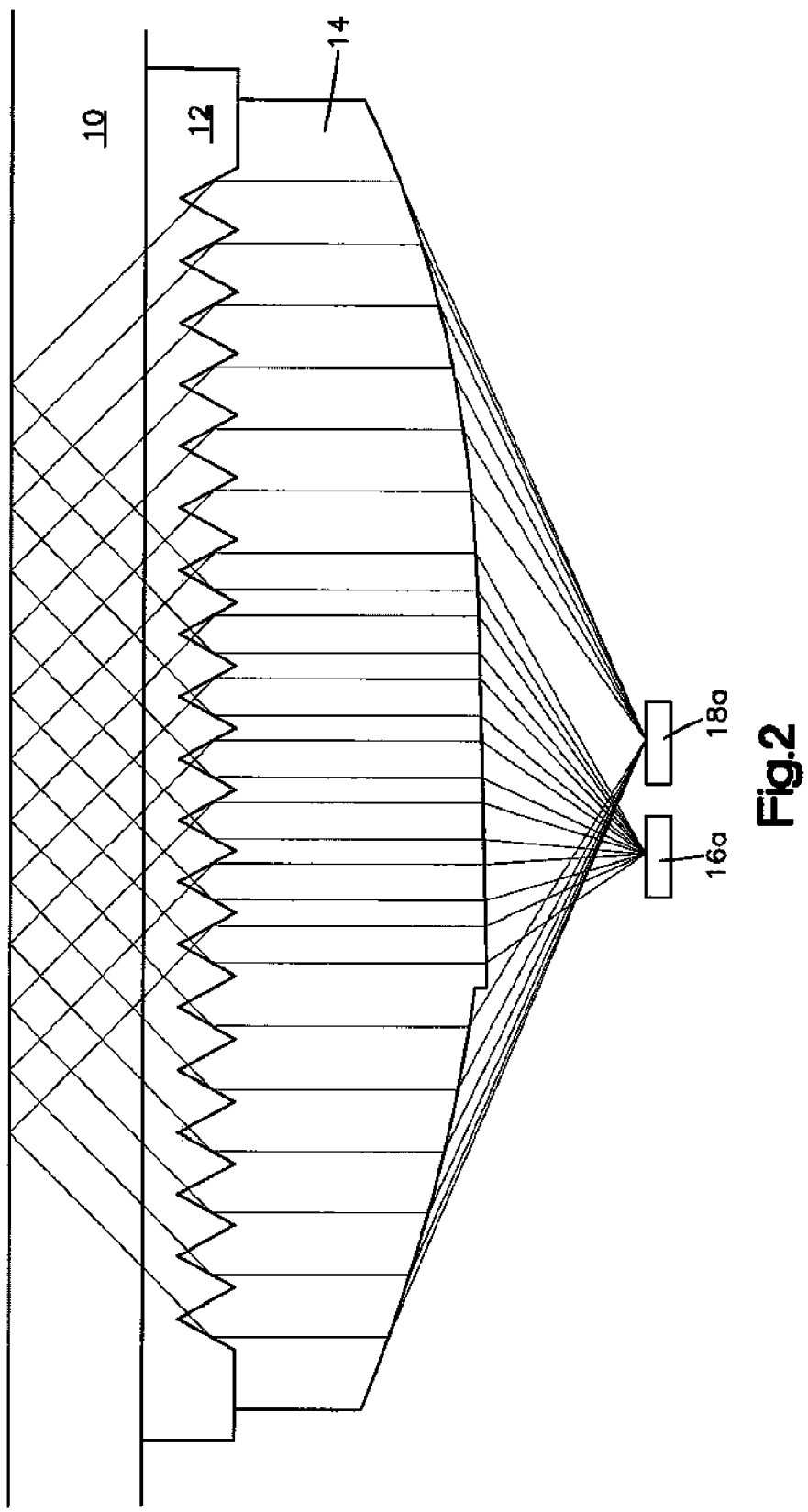

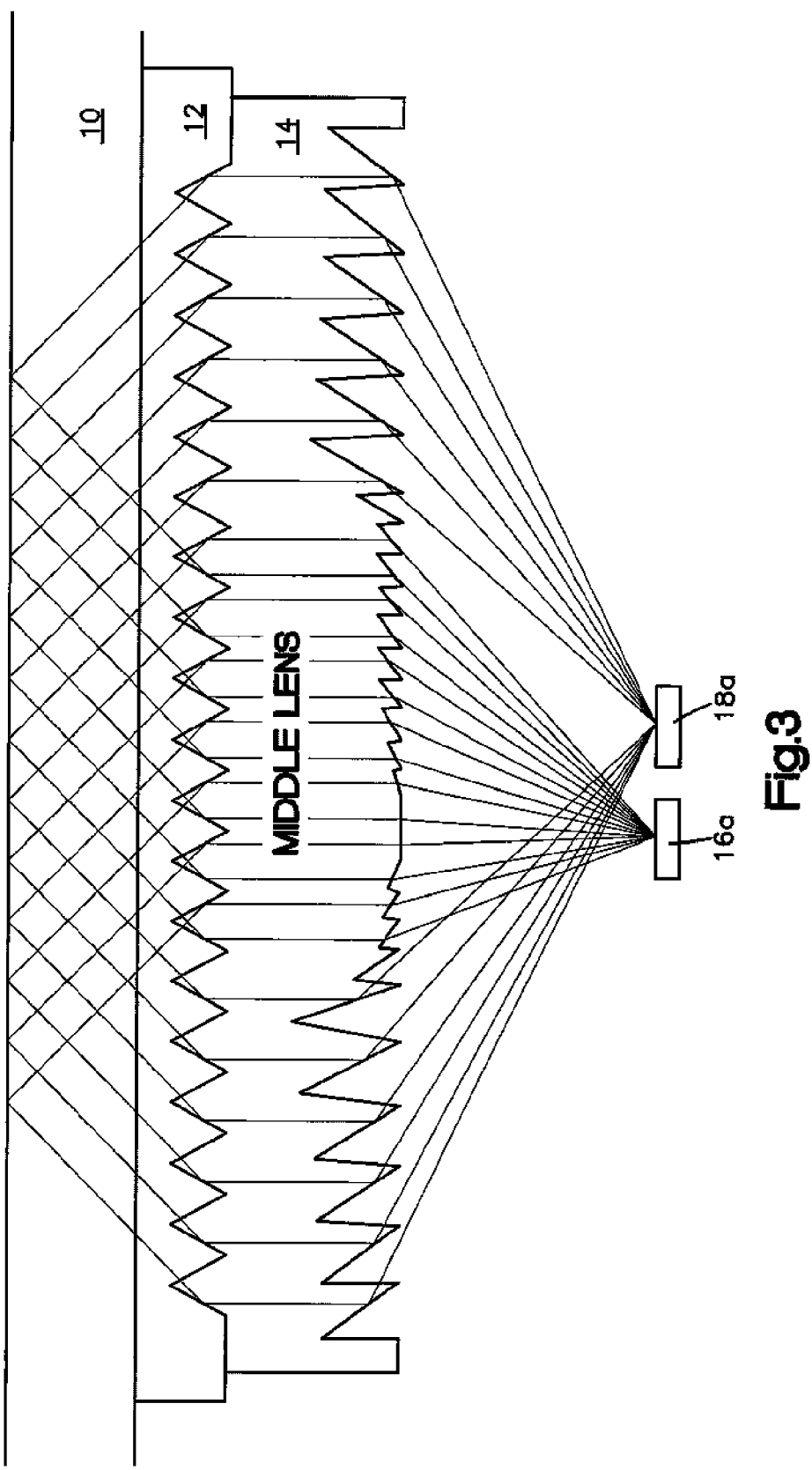

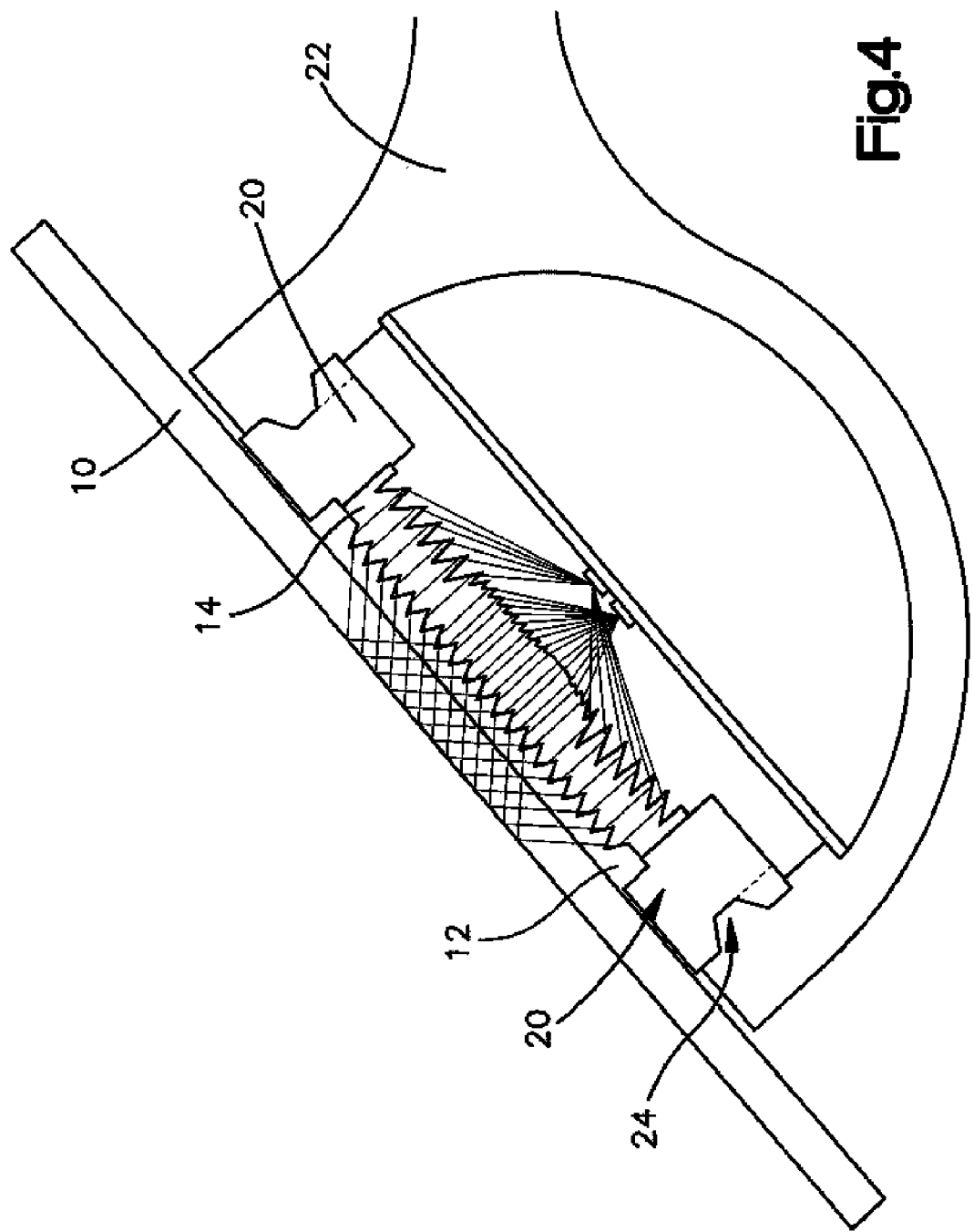

OPTICAL SENSOR DEVICE

FIELD OF THE INVENTION

The invention relates to an optical sensor device which is adapted to be coupled to a pane, in particular a windshield of a vehicle, and which detects a wetting of the pane (rain sensor).

BACKGROUND

Sensor devices of this type are mainly used as rain sensors in motor vehicles for an automatic actuation of the windshield wipers. They are based, in the final analysis, on the detection of a wetting of the pane owing to a reduction of the amount of light that is totally reflected on the internal surface of the pane. Particularly compact designs of optical sensor devices may be achieved by using Fresnel lenses.

SUMMARY

The present invention is a further development of the concept of using Fresnel structures to reduce the structural space, accompanied by a simultaneous maximum utilization of the light made available by a light source.

The optical sensor device according to the invention has at least one light emitter, at least one light receiver, and rotationally symmetrical Fresnel prism structures which are adapted to be coupled on a first side to a pane, in particular a windshield of a vehicle, and which on a second, opposite side take up light from the light emitter, couple it into the pane and, after a total reflection on an internal surface of the pane, direct it onto the light receiver. This principle allows a variety of embodiments to be realized, all of which distinguish themselves by an extremely compact design and an optimized utilization of the light made available by the light emitter. The rotationally symmetrical configuration of the Fresnel prism structures results in a good controllability of the beam paths and a good exploitation of the available surface area on the pane as well as an optimum luminous efficiency.

A feature that preferably all embodiments have in common is that the light from the light emitter impinges on the Fresnel prism structures as parallel light and is reflected back as parallel light by the Fresnel prism structures. This results in well-controllable optical paths with consistently defined angles of reflection.

In all embodiments, the Fresnel prism structures are preferably coupled to the pane by a coupling layer which is made of a transparent elastic medium and, on its surface facing the Fresnel prism structures, is shaped to be complementary thereto and in close contact, and whose opposite surface engages the pane. The coupling layer can be detached from the pane again as needed. Provision is however also made for embodiments having a rigid coupling medium and in which the Fresnel prism structures remain firmly on the pane after removal of the other parts of the sensor.

Of particular advantage is an embodiment in which the Fresnel prism structures include a central portion on which the light from the light emitter impinges as a parallel light beam. The parallel light beam is split up by the prism structures into two separate coronas that overlap on the pane. The Fresnel prism structures further include a ring-shaped outer portion that surrounds the central portion and deflects the beams totally reflected on the pane onto the light receiver as parallel light. When the prism structures are accurately formed geometrically and the outer prism portions are exactly adapted to the inner prism portions, this results in the maximum possible luminous efficiency as well as in an optimum utilization of the surface area occupied on the pane.

The opposite arrangement is also possible, that is, in which the light is irradiated into the outer portions and is diverted into the central portion after being totally reflected on the pane.

In one specific implementation, the Fresnel prism structures are preferably formed on one surface of a transparent optical plate which on its opposite surface has integrally formed convex lens structures and/or Fresnel lens structures incorporated therein and/or Fresnel reflector structures incorporated therein. In case no sheet-type light emitters and light receivers are available, lenses are required in order to reshape the light of a light emitter that, by way of idealization, is assumed to be point-shaped, into a parallel light beam and to focus the parallel light that is reflected back on a receiver that, by way of idealization, is assumed to be point-shaped.

In the configuration according to the invention, the necessary lens structures or reflector structures are formed on the surface of the transparent optical plate which is opposite the Fresnel prism structures. As a consequence, no additional space is required for the lens structures.

A special advantage is achieved by integrating in the optical plate a plurality of optical systems made up of Fresnel structures for a plurality of sensor units. The invention more specifically provides a rain/light sensor for vehicles which has a rain sensor unit and a light sensor unit with a shared optical plate.

One embodiment that is advantageous by design distinguishes itself in that a fastening ring is fitted to the outer periphery of the optical plate, the fastening ring being rigidly fastened on the pane and furthermore preferably including bayonet-type fastening means that serve for fastening an inside mirror.

BRIEF DESCRIPTION OF DRAWINGS

FIG. 2 shows a second embodiment of the sensor device, likewise in a schematic sectional view;

FIG. 3 shows a further embodiment of the sensor device in a schematic sectional view;

FIG. 4 shows a schematic sectional view of a sensor device which is fastened on a pane and on the outer periphery of which a mirror mounting bracket is attached;

DETAILED DESCRIPTION OF AN EXAMPLE EMBODIMENT

Figure 1:
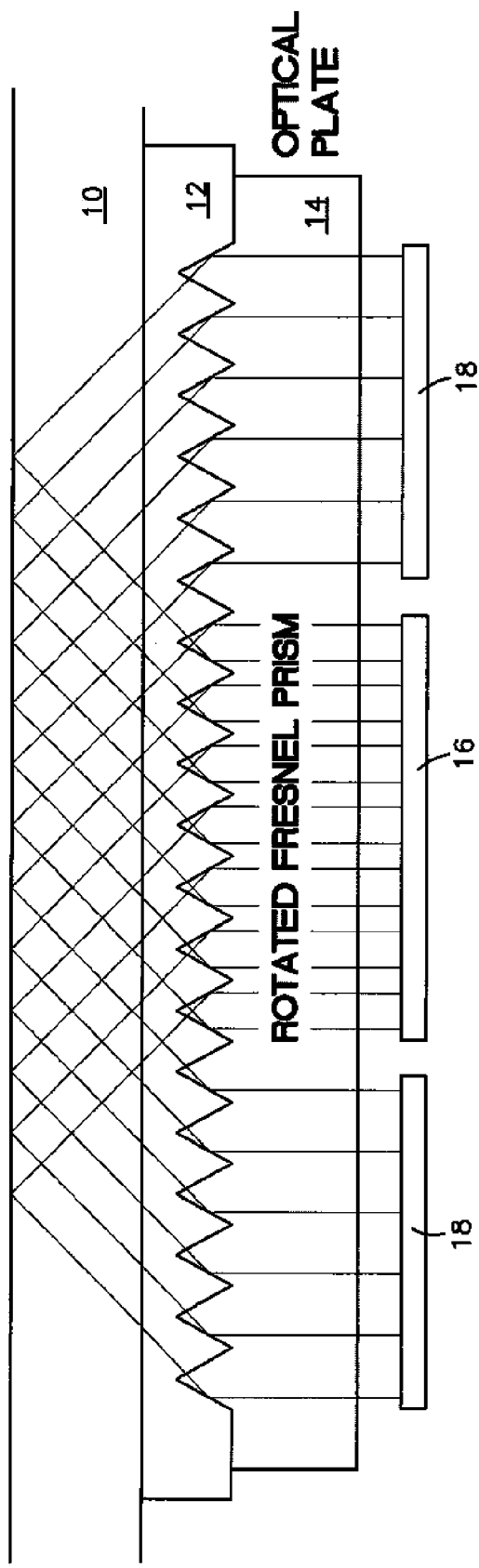
FIG. 1 shows a first embodiment of the sensor device in a schematic sectional view.

In FIG. 1, an optical plate 14 is coupled to a pane 10, in particular the windshield of a vehicle, by means of a coupling layer 12 made of a transparent elastic material. On its side facing the pane 10, the optical plate 14 is made to include Fresnel prism structures. The Fresnel prism structures are rotationally symmetrical, i.e. they have a profile that is defined by rotation of a sawtooth curve about a fixed axis. The apices visible in FIG. 1 of the sawtooth-shaped line of intersection thus constitute concentric circles when viewed from the top. A light emitter 16, which in an idealized form is assumed to be a sheet-type light radiator, emits a beam of parallel light rays vertically onto the surface, opposite the Fresnel prism structures, of the optical plate 14. The parallel light beam emitted by the light emitter 16 occupies a central portion of the optical plate 14. The parallel light beam is split up into two separate coronas at the symmetrical sawtooth-shaped flanks of the Fresnel prism structures. The individual light rays of these coronas form an angle of approximately 45 degrees with the pane 10. The light rays of the two coronas overlap on the pane 10 and are totally reflected on the external inner surface thereof and directed against the outer ring-shaped portion of the Fresnel prism structures where they are deflected as parallel light beams and vertically emerge from the optical plate. The light emitter 16 is surrounded by a ring-shaped light receiver 18 which in this case is assumed to be flat. The coupling layer 12 forms an elastic cushion which on its side facing the optical plate 14 is shaped so as to be complementary to the Fresnel prism structures and is in engagement therewith. On the opposite side, the coupling layer 12 is permanently or detachably fastened to the inside surface of the pane 10.

The embodiment according to FIG. 2 differs from that according to FIG. 1 merely in the configuration of the optical plate 14, which on its surface facing away from the Fresnel prism structures is shaped to form convex lenses. In a central portion, the convex lens takes up the light originating from a light emitter 16a that is assumed to be point-shaped and reshapes this light into a parallel light beam. In an outer peripheral portion, the convex lens is shaped such that it focuses the light which is deflected after a total reflection on the pane 10 and is then deflected on the Fresnel prism structures, on a light receiver 18a that is assumed to be point-shaped.

The embodiment according to FIG. 3 differs from the one according to FIG. 2 in that in the central portion the lens is used as a Fresnel lens, and in the outer peripheral portion a Fresnel reflector structure is used instead of a convex lens.

FIG. 4 shows a further development of the design of the embodiment according to FIG. 3. The further development consists in that a fastening ring 20 is fitted to the outer periphery of the optical plate 14. The fastening ring 20 may be permanently attached to the pane 10, in particular by an adhesive joint. The fastening ring 20 has not only the task of holding the sensor device in engagement with the inside surface of the pane 10 but, in addition, it has the function of a mount to which a mirror baseplate 22 of an inside mirror may be fastened. Fastening is preferably effected using bayonet-type fastening means 24.

Figure 5A:
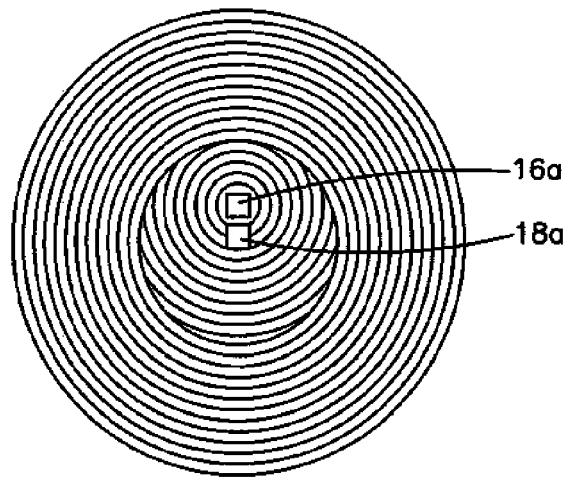
FIGS. 5a, b and c show top views onto different embodiments of the Fresnel structures.

As is illustrated in FIGS. 5a, b, c, various geometric configurations of the Fresnel structures are possible. In all embodiments, a light emitter 16a is located in the central portion. Corresponding to the embodiments shown in FIGS. 2 and 3, in FIG. 5a the light receiver 18a is arranged adjacent to the light emitter 16a.

Figure 5B:
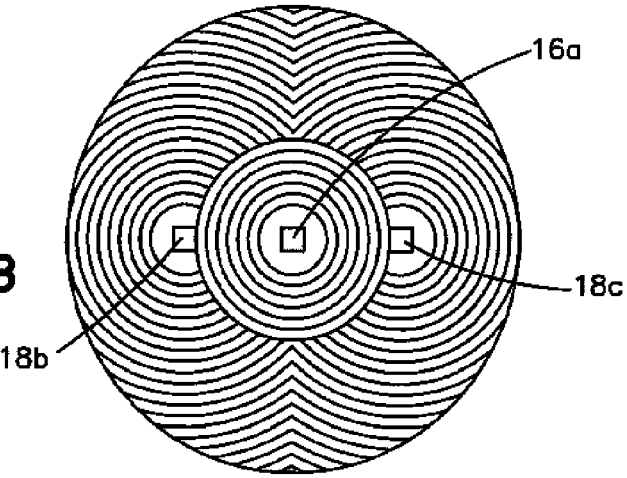

Deviating therefrom, in FIG. 5b two light receivers 18b and 18c are arranged on either side of the light emitter 16a, and the outer reflector structures are oriented to these light receivers accordingly.

Figure 5C:
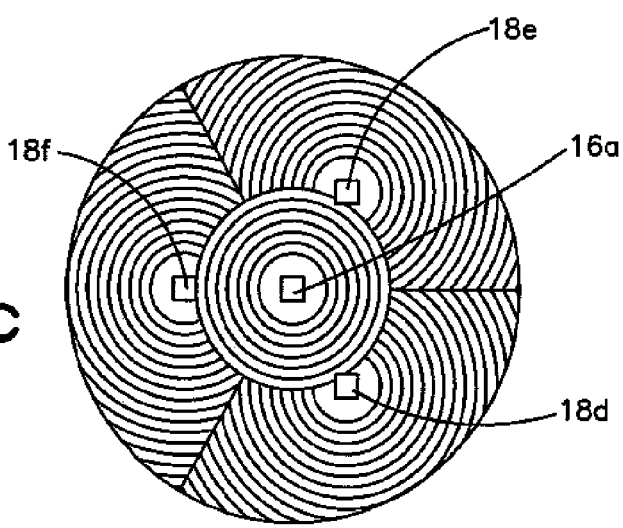

In a further development of this concept, in the embodiment according to FIG. 5c three light receivers 18d, 18e and 18f are arranged around the central light emitter 16a, and the reflector structures are oriented to these light receivers accordingly.

The design as described of the sensor device is suitable for use as a rain sensor. It is preferably integrated in a shared optical plate together with a further sensor unit, in particular a light sensor. In this way, a rain/light sensor is obtained for controlling the wiper system and the lighting system in a vehicle. A suitable light sensor will now be described below with reference to FIG. 6.

Figure 6:
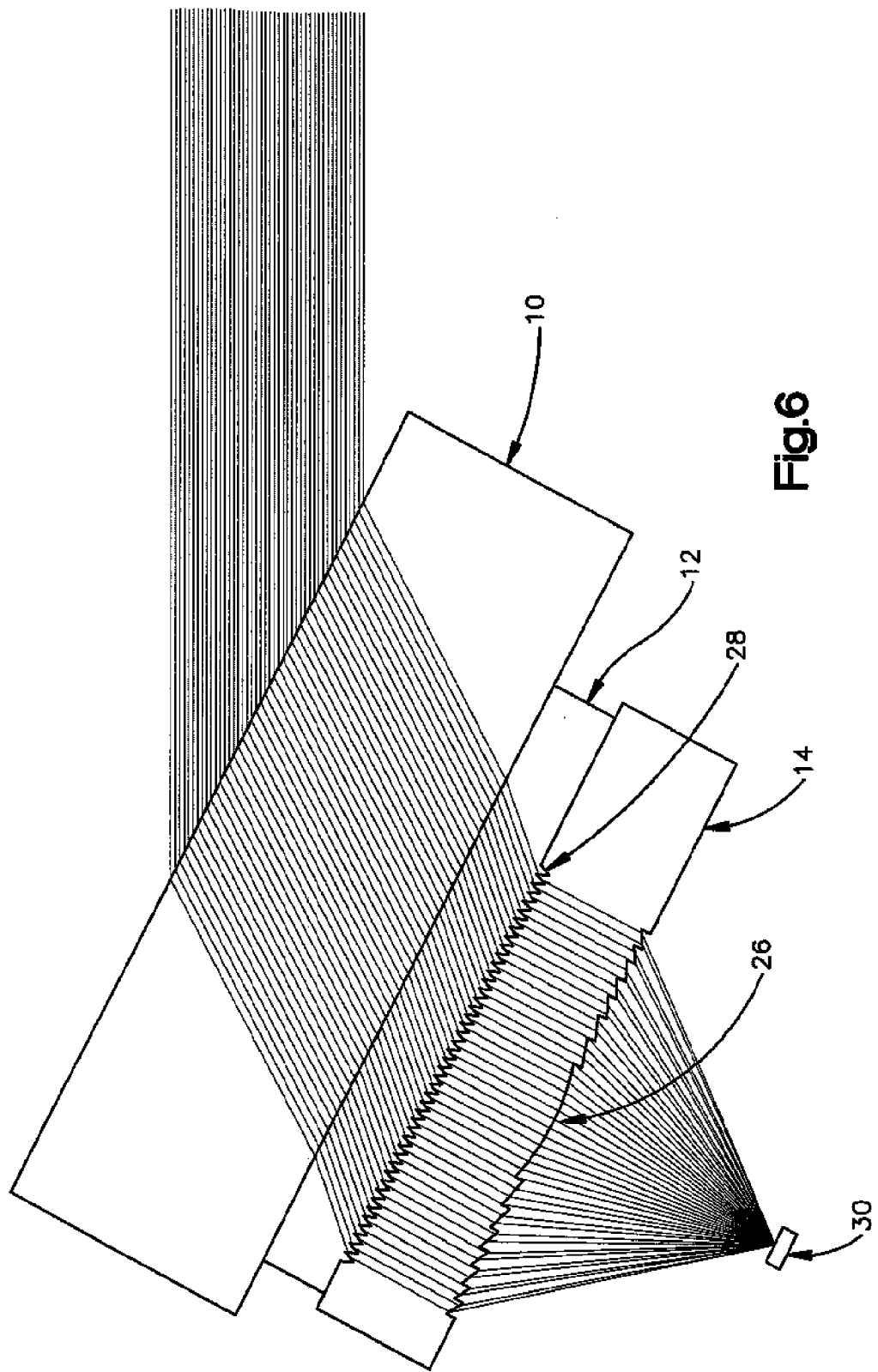
FIG. 6 shows a schematic sectional view of a light sensor.

In FIG. 6 the optical plate 14 mounted to the pane 10 by means of the coupling layer 12 comprises a further optical system for a second sensor unit which involves a direction-sensitive daylight sensor. The optical plate 14 includes a Fresnel lens structure 26 and, in opposition thereto, a corresponding Fresnel reflector structure 28. A light receiver 30 is placed in the focal point of the Fresnel lens structure 26. The daylight sensor is sensitive to light which is incident on the windshield 10 horizontally and, upon incidence on the windshield, is refracted downward at an angle to impinge on the Fresnel reflector structure 28 through the coupling layer 12. The Fresnel reflector structure 28 diverts the light beams and directs them perpendicularly through the optical plate 14 onto the Fresnel lens structure 26, which focuses the light on the light receiver 30.

Although the invention has been described hereinabove with reference to a specific embodiment, it is not limited to this embodiment and no doubt further alternatives will occur to the skilled person that lie within the scope of the invention as claimed.

The invention claimed is:

1. An optical sensor device comprising
at least one light emitter,
at least one light receiver, and
an optical plate that includes rotationally symmetrically shaped Fresnel prism structures which are adapted to be coupled on a first side to a windshield pane of a vehicle, and which on a second, opposite side are configured to take up light from the light emitter, couple the light taken up from the light emitter into the pane and, after a total reflection on an internal surface of the pane, direct said light onto the light receiver.

2. The sensor device according to claim 1, wherein the Fresnel prism structures have a profile defined by rotation of a saw-tooth curve about an axis.

3. The sensor device according to claim 2, wherein the teeth of the saw-tooth curve are symmetrical in shape.

4. The sensor device according to claim 1, wherein the light from the light emitter impinges on the Fresnel prism structures as parallel light and is directed onto the light receiver as parallel light.

5. The sensor device according to claim 1, wherein the Fresnel prism structures are detachably coupled to the pane by a coupling layer which is made of a transparent elastic medium and is shaped on its surface facing the Fresnel prism structures to be complementary to the Fresnel prism structure and on its opposite surface engages the pane.

6. The sensor device according to claim 1, wherein the Fresnel prism structures are coupled to the pane by a coupling layer made of a transparent rigid medium.

7. The sensor device according to claim 1, wherein the Fresnel prism structures include a central portion on which the light from the light emitter impinges as a parallel light beam which is split up by the prism structures into two separate coronas that overlap on the pane, and a ring-shaped outer portion that surrounds the central portion and deflects the beams totally reflected on the pane onto the light receiver as parallel light.

8. The sensor device according to claim 7, wherein the individual rays of the two coronas are inclined at an angle of approximately 45 degrees in relation to the surface of the pane.

9. The sensor device according to claim 1, wherein the Fresnel prism structures include an outer portion on which the light from the light emitter impinges as a parallel light beam, and a central portion that deflects the beams totally reflected on the pane onto the light receiver as parallel light.

10. The sensor device according to claim 1, wherein the Fresnel prism structures are formed on one surface of an optical plate made of a transparent material, the opposite surface having lens structures formed thereon which reshape light from a point-shaped light emitter into parallel light and focus parallel light of the beams totally reflected on the pane on the point-shaped light receiver.

11. The sensor device according to claim 10, wherein the lens structures are at least partly Fresnel structures.

12. The sensor device according to claim 10, wherein the light emitter and the light receiver are arranged side by side adjacent to each other.

13. The sensor device according to claim 10, wherein a centrally arranged light emitter is surrounded by a plurality of light receivers.

14. The sensor device according to claim 10, wherein bayonet-type fastening means for an inside mirror are fitted to the outer periphery of the optical plate.

15. The sensor device according to claim 10, wherein the optical plate has a plurality of optical systems formed therein having Fresnel structures for a plurality of sensor units.

16. A rain and light sensor comprising a sensor device according to claim 15.

17. The sensor device according to claim 1, wherein the Fresnel prism structure faces the windshield pane.

18. The sensor device according to claim 1, wherein the light from the emitter impinges the Fresnel prism structure as parallel light and is split by the Fresnel prism structure into two separate coronas that overlap on the pane.

* * * * *